United States Patent [19]
Baral et al.

[11] Patent Number: 5,788,964
[45] Date of Patent: Aug. 4, 1998

[54] METHOD FOR SENSITIZATION OF CANCER CELLS FOR KILLER CELL MEDIATED LYSIS

[75] Inventors: Edward Baral, Winnipeg; Istvan Berczi, Lorette; Eva Nagy, Winnipeg, all of Canada; Lauri Kangas, Raisio, Finland

[73] Assignee: Orion-Yhtymä Oy, Espoo, Finland

[21] Appl. No.: 596,121

[22] PCT Filed: Aug. 2, 1994

[86] PCT No.: PCT/FI94/00333

§ 371 Date: Apr. 15, 1998

§ 102(e) Date: Apr. 15, 1998

[87] PCT Pub. No.: WO95/04544

PCT Pub. Date: Feb. 16, 1995

Related U.S. Application Data

[62] Division of Ser. No. 103,519, Aug. 9, 1993, abandoned.

[51] Int. Cl.$^6$ .......................... A01N 63/00; A61K 39/00; A61K 39/38; A61K 9/36
[52] U.S. Cl. .................... 424/93.71; 424/184.1; 424/198.1; 424/479; 424/488; 424/493; 424/499; 435/7.23
[58] Field of Search ................... 424/93.71, 184.1, 424/198.1, 479, 488, 499, 493; 435/7.23

[56] References Cited

U.S. PATENT DOCUMENTS

| | | | |
|---|---|---|---|
| 5,024,833 | 6/1991 | Del Blanco | 424/85.4 |
| 5,057,423 | 10/1991 | Hiserodt et al. | 435/240.23 |
| 5,189,212 | 2/1993 | Ruenitz | 562/468 |

FOREIGN PATENT DOCUMENTS 0 589 039   3/1994   European Pat. Off.

OTHER PUBLICATIONS

The Merck Index, 11th edition, pp. 373, 1430, and 1504, 1989.

Osband et al. "Problems in the invetigational study and clinical use of cancer immunotherapy" Immunotherapy, p. 1930–195, 1990.

Chaterjee et al. "Idiotype antibody immunotherapy of cancer" Cancer Immunol. Immunother. vol. 38, pp. 75–82, 1994.

Mallmann et al. "Effect of Tamoxifen and high–does medroxyprogesterone acetate (MPA) on cell mediated immune functions in breast cancer patients" Meth. Find. Exp. Clin. Pharmocol. vol. 12, No. 10, pp. 699–706, 1990.

Berry et al. "Modulation of natural killer cell activity by Tamoxifen in stage I post–menopausal breast cancer" Eur. J. Cancer Clin. Oncol., vol. 23, No. 5, pp. 517–520, 1987.

Kangas et al. "Additive and synergistic effects of a novel antiestrogen, toremifene (Fc-1157a), and human interferons on estrogen responsive MCF-7 cells in vitro" Med. Biol. vol. 63, pp. 187–190, 1985.

Robertson et al. "Biology and clinical relevance of human natural killer cells" Blood, vol. 76, No. 12, pp. 2421–2438, 1990.

Michael Andersson et al., "Incidence of New Primary Cancers After Adjuvant Tamoxifen Therapy and Radiotherapy for Early Breast Cancer", J. Natl. Cancer Institute, vol. 83, No. 14, Jul. 17, 1991.

R.I. Freshney, "B. Monolayer Cultures", Short Term Culture of Human Tumours. Techniques and Clinical Applications, PP. Dendy, ed. Academic Press, London, 1976.

Shigeyoshi Fujimoto et al., "Development of Specific Immunotherapy for Cancer", (translation from abstract), Human Cell, 5, 247–55, 1992.

Tenho Hietanen et al., "High Dose Toremifene (240 mg daily) is Effective as First Line Hormonal Treatment in Advanced Breast Cancer –An Ongoing Phase II Multicenter Finnish–Latvian Cooperative Study", Breast Cancer Research and Treatment, 16, S–37–40, 1990.

Steven A. Rosenberg, M.D. et al., "A Progress Report on the Treatment of 157 Patients with Advanced Cancer Using Lymphokine–Activated Killer Cells and Interleukin–2 or High Dose Interleukin–2 Alone", New England Journal of Medicine, vol. 316, No. 15, Apr. 1987, pp. 889–897.

Ichiro Yoshino et al., "Cytolytic Potential of Peripheral Blood T–Lymphocytes Following Adoptive Immunotherapy with Lymphokine–Activated Killer Cells and Low–Dose Interleukin–2", Cancer Research, 51, 1494–1498, Mar. 1, 1991.

Herbert C. Hoover, Jr. et al., "Adjuvant Active Specific Immunotherapy for Human Colorectal Cancer: 6.5 Year Median Follow–up of a Phase III Prospectively Randomized Trial", Journal of Clinical Oncology, vol. 11, No. 3, (Mar.), 1993: pp. 390–399.

Alfred E. Chang et al., "Clinical Observations on Adoptive Immunotherapy with Vaccine–primed T–Lymphocytes Secondarily Sensitized to Tumor in Vitro", Cancer Research, 53, 1043–1050, Mar. 1, 1993.

Philip O. Livingston, "Construction of Cancer Vaccines with Carbohydrate and Protein (Peptide) Tumor Antigens", Current Opinion in Immunology, 4,5, 624–9, 1992.

Masashi Komatsumoto et al., "The Improved Effects of Specific Active Immunotherapy on a Rat Fibrosarcoma by Antitumor Drugs", Cancer Immunology Immunotherapy, 33, 279–284, 1991.

(List continued on next page.)

*Primary Examiner*—Lila Feisee
*Assistant Examiner*—Yvonne Eyler
*Attorney, Agent, or Firm*—Burns, Doane, Swecker & Mathis, L.L.P.

[57] ABSTRACT

The invention relates to a method of sensitizing cancer cells for a killer cell mediated lysis which involves administering to a patient an effective amount of antiestrogen and killer cells either jointly or sequentially, wherein the killer cells are selected from the group of NK cells, LAK cells and CTL cells and the antiestrogen is selected from the group of triphenylethylene class antiestrogens, such as tamoxifen or toremifene or their pharmaceutically acceptable salt.

25 Claims, 10 Drawing Sheets

OTHER PUBLICATIONS

Kroum T. Kassabov et al., "Inhibition of Spontaneous Pulmonary Metastases of Lewis Lung Carcinoma by Oral Treatment with Respivax and Broncho–Vaxom", Cancer Immunology Immunotherapy, 33, 307–313, 1991.

Mary Nel Saarloos et al., "Effects of Cancer Immunotherapy with Indomethacin and Interleukin-2 on Murine Hemopoietic Stem Cells", Cancer Research, 52, 6452–6462, Dec. 1, 1992.

Hisashi Aso et al., "Impaired NK Response of Cancer Patients to IFN–α but Not to IL–2: Correlation with Serum Immunosuppressive Acidic Protein (IAP) and Role of Suppressor Macrophage", Microbiological Immunology, vol. 36, (10), 1087–1097, 1992.

Teruhiro Utsugi et al., "Comparative Efficacy of Liposomes Containing Synthetic Bacterial Cell Wall Analogues for Tumoricidal Activation of Monocytes and Macrophages", Cancer Immunology Immunotherapy, 33, 287–292, 1991.

Mark R. Albertini et al., "Influence of Estradiol and Tamoxifen on Susceptibility of Human Breast Cancer Cell Lines to Lysis by Lymphokine–Activated Killer Cells", Journal of Immunotherapy, vol. 11, No. 1, pp. 30–39, 1992.

Benjamin Kim, M.D., et al., "Tamoxifen Potentiates in Vivo Antitumor Activity of Interleukin-2", Surgery, vol. 108, No. 2, pp. 139–145, Aug. 1990.

Stephen E. Ettinghausen et al., "Recombinant Interleukin 2 Stimulates in Vivo Proliferation of Adoptively Transferred Lymphokine–Activated Killer (LAK) Cells", *The Journal of Immunology*, Nov. 1985, vol. 135, No. 5, pp. 3623–3635.

John Berry et al., "Modulation of Natural Killer Cell Activity By Tamoxifen in Stage I Post–Menopausal Breast Cancer", *Eur. J. Cancer Clin Oncol.*, vol. 23, No. 5, pp. 517–520, 1987.

Bluma G. Brenner et al., "The Relationship of Chemotherapuetic and Endocrine Intervention on Natural Killer Cell Activity in Human Breast Cancer", *Cancer*, 68: pp. 482–488.

E. Robinson et al., "In vivo modualation of natural killer cell activity by tamoxifen in patients with bilateral primary breast cancer", *Cancer Immunol Immunother*, (1993) 37: 209–212.

METHOD FOR SENSITIZATION OF CANCER CELLS FOR KILLER CELL MEDIATED LYSIS

This application is a 371 of PCT/FI94/00333 which is a continuation of the U.S. application Ser. No. 08/103,519, filed Aug. 9, 1993, now abandoned.

BACKGROUND OF THE INVENTION

The invention relates to the treatment of cancer by sensitization of cancer cells by antiestrogens for lysis with killer cells, particularly with natural killer (NK) cells, lymphokine activated killer (LAK) cells and cytotoxic T lymphocytes (CTL).

The treatment of human cancer with autologous lymphokine activated killer (LAK) cells combined with recombinant-derived lymphokine, interleukin-2, has already been attempted with encouraging results (Rosenberg, 1987) as well as the treatment with activated cytotoxic T lymphocytes (CTL) (Fujimoto, 1992).

Nonsteroidal antiestrogens tamoxifen and toremifene belonging to the triphenylethylene class of compounds have gained wide therapeutic application for the treatment of estrogen receptor positive breast cancer. Tamoxifen and toremifene inhibit estrogen-induced growth by competitive antagonism of tumor estrogen receptors. Antiestrogen therapy is effective in prolonging a disease-free state and overall survival of women following primary surgery. Other well known triphenylethylene class antiestrogens are e.g. clomiphene and droloxifene (3-hydroxytamoxifen).

We have now discovered that estrogen receptor negative cancer cells are sensitized by triphenylethylene antiestrogens for lysis with NK, LAK and CTL effectors. This sensitization effect is thus not dependent on the presence of classical estrogen receptors. The use of the combination of antiestrogen treatment and killer cell therapy according to the invention is expected to significantly elevate the percentage of tumor remission and cure that has already been achieved by the above investigators with killer cells alone in a minor percentage of patients.

SUMMARY OF THE INVENTION

The invention relates to a method of sensitizing cancer cells for a killer cell mediated lysis which involves administering to a patient an effective amount of antiestrogen and killer cells either jointly or sequentially, wherein the killer cells are selected from the group of NK cells, LAK cells and CTL cells and the antiestrogen is selected from the group of triphenylethylene class antiestrogens, such as tamoxifen or toremifene or their pharmaceutically acceptable salt. Alternatively, killer cells may be induced in a host by one of known immunostimulation methods during the first treatment period and thereafter administering an effective amount of antiestrogen during the second treatment period.

DETAILED DESCRIPTION OF THE INVENTION

1. Detection of killer cells

Figure 1:
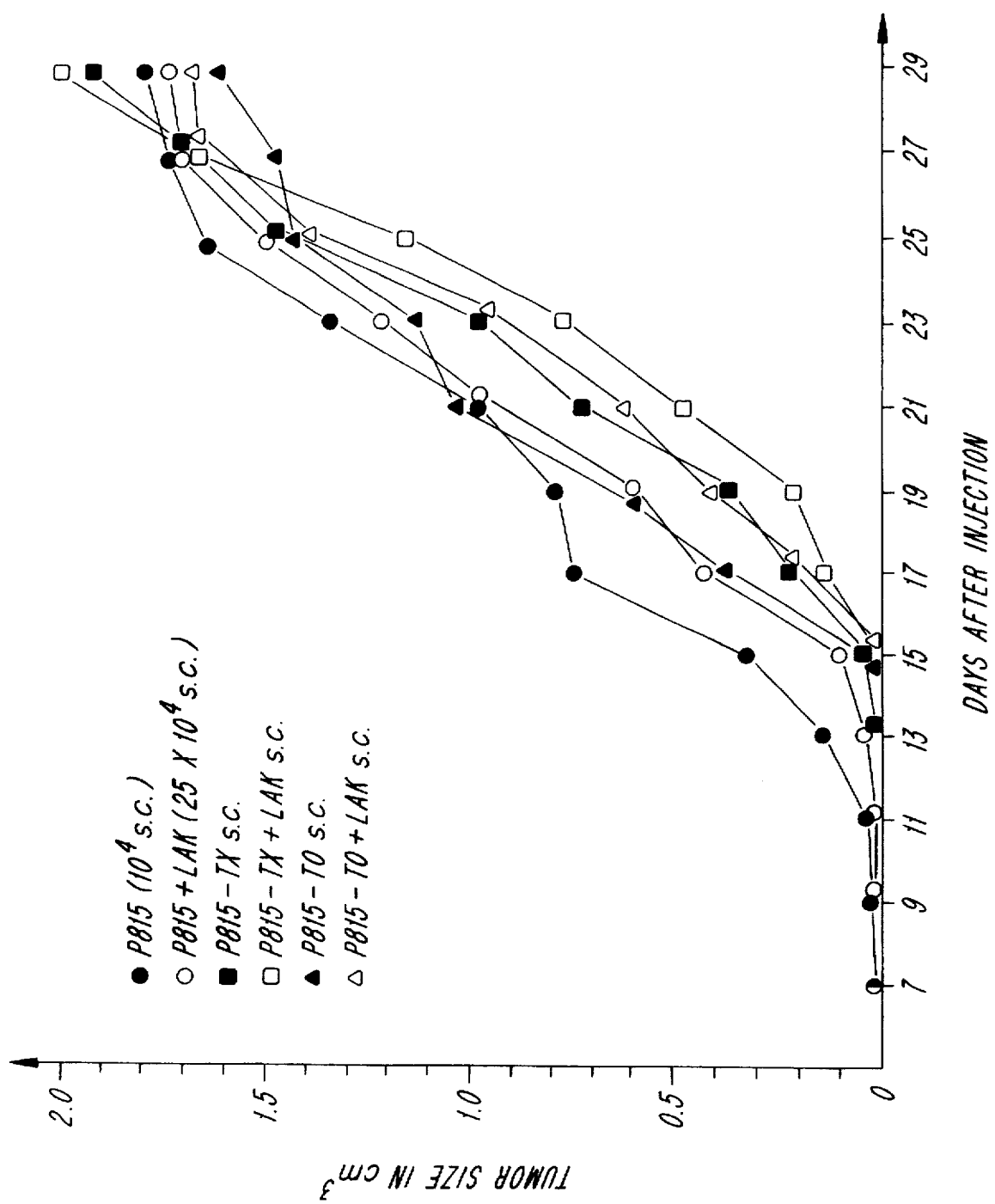
FIG. 1 is a graph of a Winn assay with untreated, tamoxifen (TX) treated and toremifene (TO) treated P815 tumor cells.

The prerequisite for success of the treatment according to the invention is the presence of killer cells (e. g. NK, LAK or CTL) capable of destroying the patient's cancer cells in the body when the adjuvant therapy with an antiestrogen, e. g. tamoxifen (TX) or toremifene (TO), is initiated. Ideally, a suspension of cells would be prepared from the patient's tumor by digestion with collagenase as described by Freshney (1976) and used as target cells. Some of the targets will then be pretreated for 4 hours with either TX or TO while others are left untreated, and both preparations are labeled with $^{51}Cr$. Patient's peripheral blood mononuclear cells depleted of adherent cells are used as effectors in $^{51}Cr$ release assay. Surplus tumor cells may be stored in tissue culture medium, such as RPMI-1640, supplemented with 10% serum (preferably autologous) and 10% dimethylsulphoxide in liquid nitrogen for later use. If this approach is not feasible, one may be able to use cell lines as targets, such as K652, which is suitable for the detection of NK activity, or lines derived from the same type of cancer the patient is suffering from. The presence of tumor infiltrating lymphocytes (TIL) in biopsy specimen may be taken as indication for the presence of host derived killer cells. Additional procedures that are used to detect cell mediated immunity and could be of use are: delayed type hypersensitivity skin reactions elicited by tumor antigen/ extract; inhibition of peripheral leukocyte migration by tumor antigen/extract; and the proliferative response of CD8+ T lymphocytes to tumor antigen/extract in vitro.

Once it has been established by any one of the above procedures that the patient harbours killer cells capable of killing his/her cancer, antiestrogen therapy will be initiated until tumor regression is achieved. If killer cells are not present they should be induced in a host by reduction of tumor burden or by immunostimulation methods as described below.

2. Reduction of tumor burden

Most patients with overwhelming tumor burden will not have detectable killer cells in their circulation. Here the first task would be to reduce tumor burden, if possible, by surgery, radiation or chemotherapy. There are numerous animal experiments and observations on patients to indicate that the reduction of tumor burden frequently leads to the appearance of killer cells, both in the circulation and in the tumor itself. Once the killer cells are detectable, the adjuvant therapy with the antiestrogen would commence.

3. Immunostimulation

If the reduction of tumor burden does not lead to the spontaneous appearance of killer cells in the patient, the stimulation of such killer cells may be attempted. Some of the approaches that can be used are listed below:

(a) Vaccination.
(b) Treatment with cyclophosphamide, which is known to inhibit suppressor immune mechanisms, and thus to enhance cellular immunity. Similarly, indomethacin interferes with the suppressive effect of macrophages.
(c) By the application of cytokines, such as interleukin-2.
(d) By the use of adjuvants stimulating cell mediated immunity such as muramyl peptide and synthetic bacterial wall analogues (Utsugi et al, 1991).
(e) By dietary factors, such as vitamin A (Gergely et al, 1988).

Suitable vaccination procedures are described by Livingston, 1992; Chang et al, 1993 and Hoover et al 1993. Cyclophosphamide treatment is described, for example, by Komatsumoto et al, 1991 and Kassabov and Stoychkov, 1991. Indomethacin treatment is described, for example, by Saarloos et al, 1993 and Aso et at, 1992.

The usual therapeutic dose for cyclophosphamide is 50 mg daily and for indomethacin 50 mg daily. Cytokines, such as interleukin-2 (IL-2), may also be used for immunostimulation as described e. g. in Yoshino et al. (1991). Yoshino et al. treated patients with low dose IL-2 ($2 \times 10^6$ Japan reference units s. c. initially, which dose was decreased to half on each consecutive day for 6 days) which resulted in significant activation of NK and LAK cells.

Once killer cells have been induced, target sensitization with antiestrogen therapy would commence.

4. Joint Therapy with Killer Cells

Administering in vitro activated killer cells of NK, LAK or CTL type and antiestrogen either jointly or sequentially is within the scope of the invention. Antiestrogen is selected from the group of triphenylethylene antiestrogens. The preferred antiestrogen is toremifene or tamoxifen or their pharmaceutically acceptable salt. Our experiments show that such combination therapy has a definite advantage in comparison with either drug treatment or killer cell therapy alone. According to our experiments target cell sensitization is optimally exploited at the stage when killer cells are already generated by the patient, or alternatively, when the killer cells are applied jointly with the drugs.

For the generation of LAK cells, patient's mononuclear lymphocytes are cultured with interleukin-2. The mononuclear lymphocytes are collected as described in Rosenberg et al (1987). The procedure can be used in order to collect about $1 \times 10^8$ to $1 \times 10^{11}$ mononuclear cells per patient. The lymphocytes can then be separated from the adherent cells using known procedures. The resulting mononuclear lymphocytes are cultured in any appropriate media such as RPMI-1640 supplemented with human recombinant interleukin-2, for example at 37° C. for three to five days. The resulting LAK cells are isolated and suspended in media suitable for intravenous infusion into the patient. The LAK cells are administered preferably once every day or every other day for from one to five daily doses. Preferably from $1 \times 10^8$ to $1 \times 10^{10}$ LAK cells are administered daily on each of three days over a period of from 3 to 10 days. The patient may require from one to four such regimens sequentially. NK and CTL cells may be administered in a similar fashion. Further guidelines for NK and CTL therapy may be obtained from the publications of Rosenberg et al. (1987) and Fujimoto (1992).

The doses for TX and TO and treatment schedule that are currently in use would be applied in therapy according to the invention. For TX an suitable oral dose is 20–40 mg given daily (Anderson et al. , 1981). The suitable oral dose for TO is 40–60 mg, but can be as high as 240 mg daily (Hietanen et al. , 1990). Preferably the antiestrogen treatment is started as soon as the killer cells are generated or infused into the patient. The antiestrogen therapy and killer cell therapy are then maintained jointly, optimally until the complete cure of the patient. It is also within the scope of the invention to apply the antiestrogen therapy and killer cell therapy sequentially, i. e. killer cell therapy is commenced immediately after discontinuation of antiestrogen therapy. However, the joint therapy is the preferred procedure.

In conclusion, the treatment procedure of using TX or TO to enhance cell mediated host defense according to the invention is preferably as follows:

(a) Tests are performed for the detection of killer cells in the patient;
(b) if killer cells are not present they are induced by known methods, or
(c) killer cells are generated in vitro and infused to the patient;
(d) TX or TO adjuvant therapy is applied as soon as the killer cells are generated or infused into the patient, preferably after the determination of the sensitizing effect of these drugs on the target cell in question for lysis by the effector cells available;
(e) during therapy with the sensitizing drugs the patient is followed closely for effectiveness.

Various modifications can be made in the therapeutic method of the present invention without departing from the spirit and scope thereof. The embodiments described herein are for the purpose of illustrating the invention but are not intended to limit it.

Example 1.

The effect of toremifene (TO) and tamoxifen (TX) on target cell lysis by natural killer (NK) cells, lymphokine activated killer (LAK) cells, and cytotoxic T lymphocytes (CTL) was studied. Rat spleen cells were used as effector cells either without activation (NK cells), or after treatment with human IL-2 (LAK), or after stimulation with the Nb2 rat lymphoma in mixed cultures (CTL). The Yac-1 murine lymphoma was used as a target for NK cells, the P815 mastocytoma for LAK cells and Nb2 cells for CTL. Target and effector cells were pretreated with TO or TX, at concentrations from 1 nM to 5 µM, for 4 hours and then washed. Target cells were labeled with $^{51}Cr$ for 1 hr, then washed. The specific $^{51}Cr$ release was determined after 4 hours of incubation at 37° C., 5% $CO_2$ (target/effector 1:25). The results presented in Tables 1–3 show that TO and TX enhanced target cell lysis in a dose dependent fashion with NK, LAK or CTL effectors, if the target cells were treated for 4 h prior to the cytotoxic reaction. The pretreatment of effector cells had no such enhancing effect, but TO or TX treated effectors lysed treated targets as efficiently as did nontreated effectors.

TABLE 1

The effect of tamoxifen (TX) and toremifene (TO) on NK cell mediated cytotoxicity.

| | | Percent specific $^{51}Cr$ release | | |
|---|---|---|---|---|
| n | Treatment | Target treated | Effector treated | Both treated |
| 7 | none | 10 ± 1 | 10 ± 1 | 10 ± 1 |
| 4 | TX 1 µM | 74 ± 2 | 1 ± 0.2 | 77 ± 2 |
| 4 | TX 100 nM | 68 ± 1 | 0.3 ± 0 | 74 ± 2 |
| 2 | TX 10 nM | 61 ± 1 | 0 ± 0 | 62 ± 1 |
| 2 | TX 1 nM | 30 ± 2 | 0 ± 0 | 42 ± 2 |
| 4 | TO 5 µM | 65 ± 3 | 1.3 ± 0.7 | 68 ± 3 |
| 4 | TO 1 µM | 54 ± 3 | 1.0 ± 0.4 | 59 ± 3 |

TABLE 1-continued

The effect of tamoxifen (TX) and toremifene (TO)
on NK cell mediated cytotoxicity.

| | | Percent specific $^{51}$Cr release | | |
|---|---|---|---|---|
| n | Treatment | Target treated | Effector treated | Both treated |
| 4 | TO 100 nM | 48 ± 2 | 0.3 ± 0 | 52 ± 1 |
| 3 | TO 10 nM | 40 ± 1 | 0 ± 0 | 41 ± 2 |
| 2 | TO 1 nM | 25 ± 3 | 0 ± 0 | 30 ± 2 |

Target cells: Yac-1 murine lymphoma
Effector cells: Spleen lymphocytes of female Fishner rats

TABLE 2

The effect of tamoxifen (TX) and toremifene (TO)
on target cell destruction by cytolytic
lymphocytes generated in mixed cultures

| | | Percent specific $^{51}$Cr release | | |
|---|---|---|---|---|
| n | Treatment | Target treated | Effector treated | Bath treated |
| 2 | none | 11 ± 1 | 11 ± 1 | 11 ± 1 |
| 2 | TX 1 μM | 76 ± 2 | 8 ± 0 | 82 ± 2 |
| 2 | TX 100 nM | 45 ± 2 | 5 ± 1 | 52.5 ± 1.5 |
| 2 | TO 5 μM | 62 ± 2 | 5.5 ± 0.5 | 61 ± 1 |
| 2 | TO 1 μM | 52 ± 2 | 3.5 ± 0.5 | 54 ± 2 |
| 2 | TO 100 nM | 31 ± 1 | 1.5 ± 0.5 | 35 ± 3 |
| 2 | TO 10 nM | 25 ± 1 | 0 ± 0 | 22 ± 2 |
| 2 | TO 1 nM | 16 ± 1.5 | 0 ± 0 | 14.5 ± 3.5 |

Target cells: Nb2 rat lymphoma
Effector cells: Cytotoxic T-lymphocytes (CTL) generated in mixed cultures, harvested on day 5
Responder: Spleen cells of Fischer rats. Stimulator: Nb2 cells (thymic lymphoma of Noble rats).

TABLE 3

The effect of tamoxifen (TX) and toremifene (TO)
on LAK cell mediated cytotoxicity.

| | | Percent specific $^{51}$Cr release | | |
|---|---|---|---|---|
| n | Treatment | Target treated | Effector treated | Both treated |
| 3 | none | 10 ± 2 | 10 ± 2 | 10 ± 2 |
| 2 | TX 1 μM | 78 ± 0 | 2 ± 0 | 84 ± 1 |
| 1 | TX 100 nM | 72 ± 0 | 2 ± 0 | 82 ± 0 |
| 3 | TO 5 μM | 75 ± 4 | 2 ± 0.3 | 77 ± 2 |
| 3 | TO 1 μM | 66 ± 3 | 0 ± 0 | 70 ± 0 |
| 3 | TO 100 nM | 59 ± 1 | 0 ± 0 | 61 ± 1 |
| 3 | TO 10 nM | 48 ± 1 | 0 ± 0 | 50 ± 0.3 |
| 3 | TO 1 nM | 36 ± 2 | 0 ± 0 | 43 ± 2 |

Target cells: P815 (NK-resistant murine mastocytoma)
Effector cells: Spleen cells of Fischer rats were cultured in medium supplemented with 500 U/ml riL-2 for 6 days at 37° C. and 5% $CO_2$.

Example 2.

Figure 2:
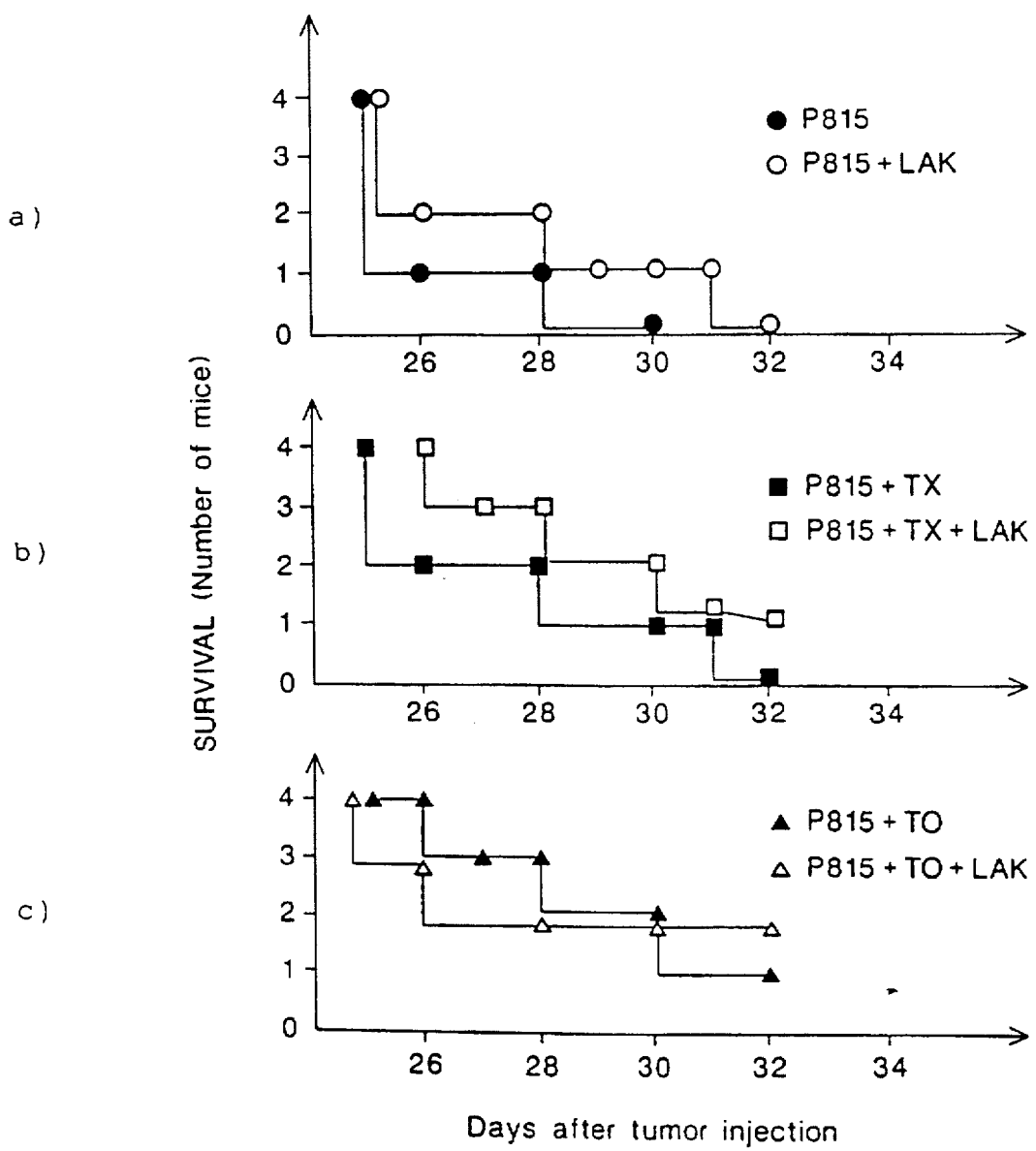
FIGS. 2a, 2b and 2c are the survival curves for the experiment of FIG. 1.

For the generation of LAK cells, $2 \times 10^6$/ml of spleen cells from female DBA/N2 mice were cultured for 5 days in RPMI-1640 medium supplemented with 10%FCS, $5 \times 10^{-5}$ M 2-mercaptoethanol and 500 U/ml of human recombinant interleukin-2 at 370C in humidified air containing 5% $CO_2$. The LAK cells generated killed, at 1:25 ratios, 10 % of P815 cells, 52 % of tamoxifen (TX) treated (1 μM, 4 h) and 51 % of toremifene (TO) treated (5 μM, 4 h) cells in the $^{51}$Cr assay. The same effector cells were then mixed with the same untreated or drug treated P815 cells at 1:25 target:effector cell ratios and injected s. c. to syngenic DBA/2 recipients (Winn assay). Groups of 4 female animals were used and tumor growth was followed until all controls succumbed to neoplasia. Further details of the experimental design and tumor size are presented in FIG. 1. In this figure only those animals that developed a tumor are included. The survival curves are presented in FIGS. 2 a, b and c.

As is obvious from the results, drug treatment alone or LAK cells alone exerted some tumor inhibition, and when both drug treatment and effector cells were applied, tumor inhibition was enhanced. For instance, tumor cells exposed to TX or LAK cells killed all the animals, whereas one animal was protected in the TX+LAK group. Pretreatment with TO protected 1 of 4 animals, whereas TO+LAK protected 2 of 4 animals. Also, it is clear from FIG. 1 that there is a marked retardation of tumor growth in the drug+LAK treated groups between days 17–23.

Example 3.

Figure 3:
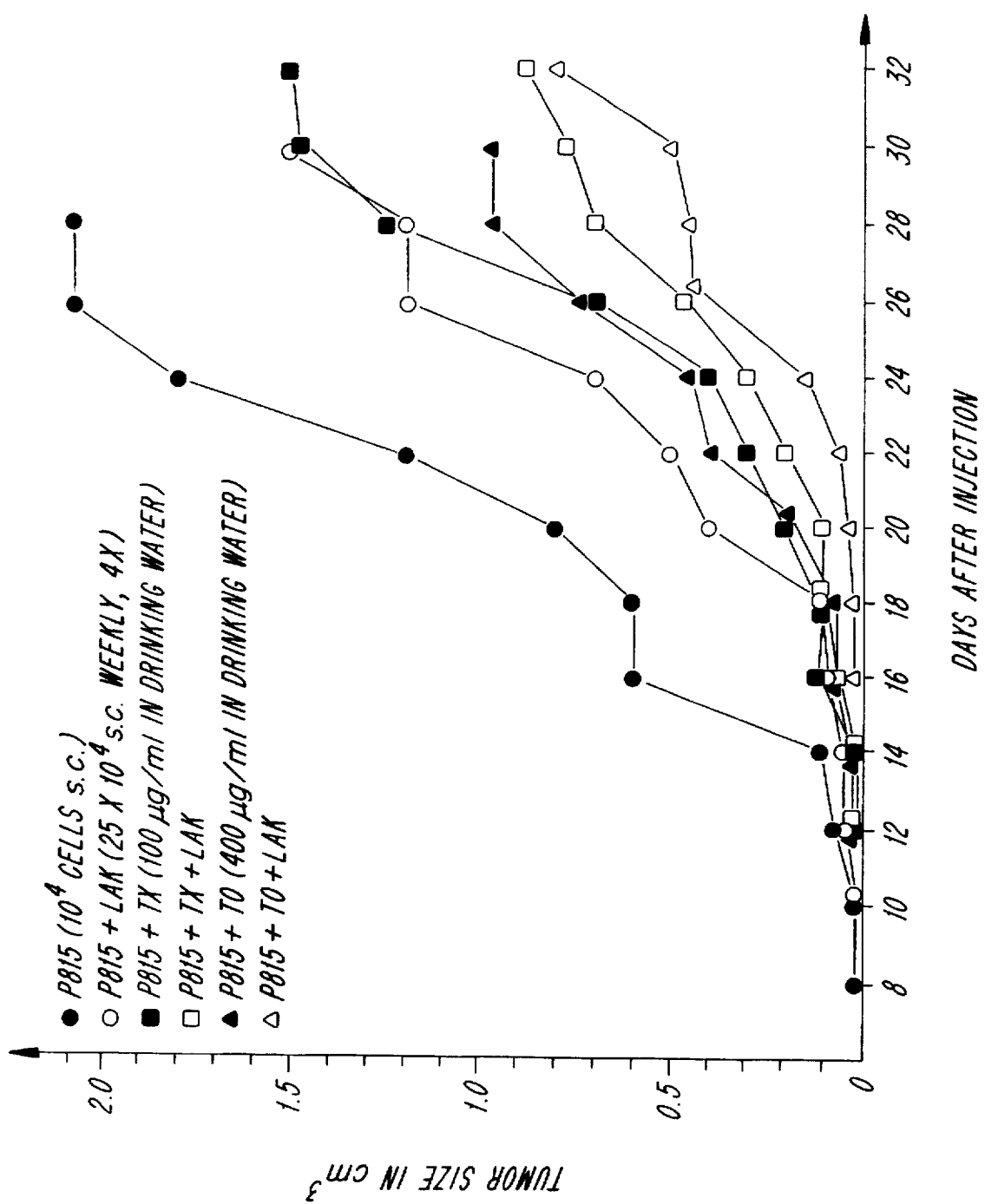
FIG. 3 is a graph of the effect of oral TX and TO treatment alone or with LAK treatment on P815 tumor growth.
Figure 4:
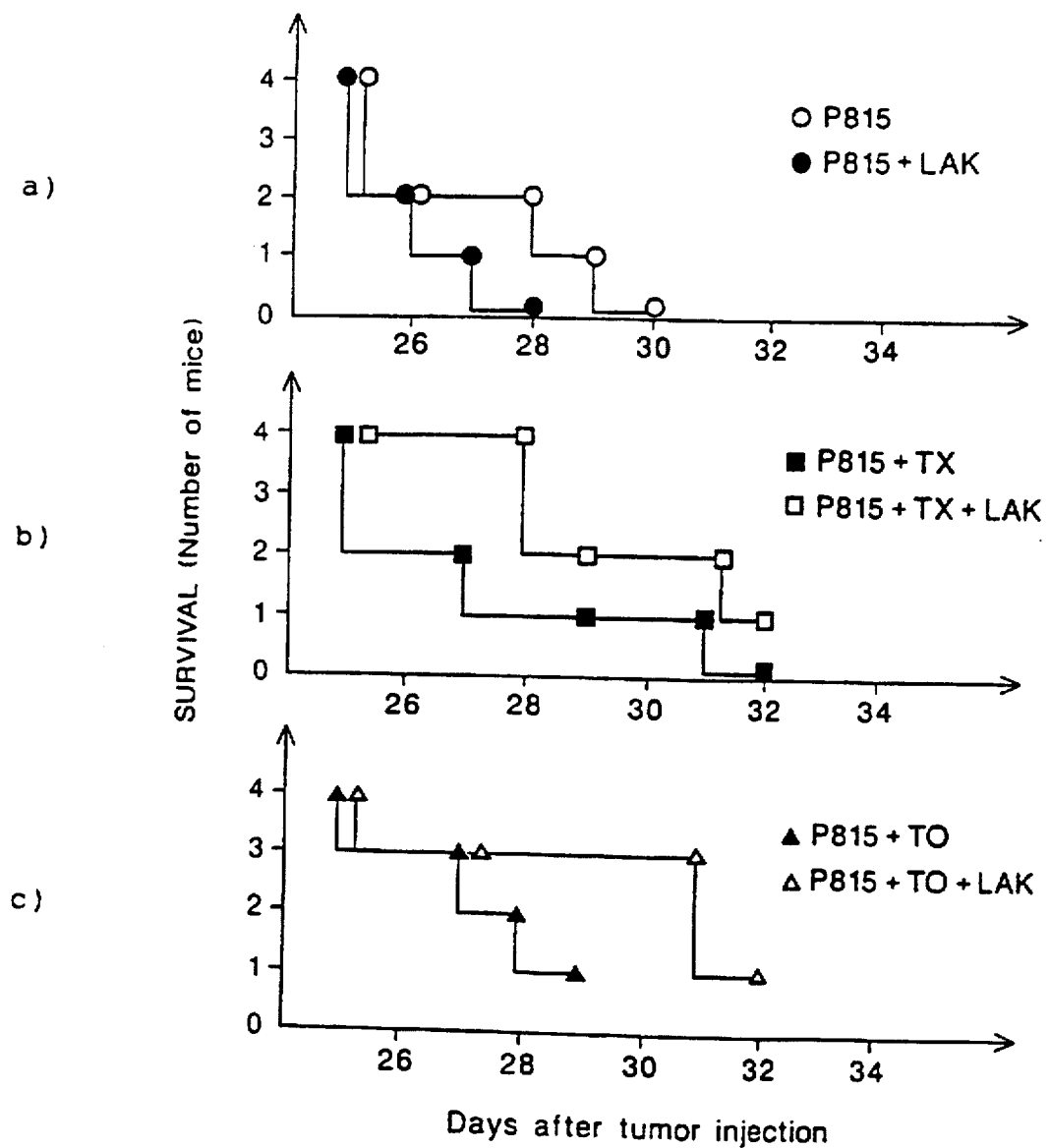
FIGS. 4a, 4b and 4c are the survival curves for the experiment of FIG. 3.

In the previous experiment there was only a brief exposure of the tumor cells to the drug (4 h) and to LAK cells, which explains that tumor retardation was limited to the early period in those animals which eventually grew the tumor. In the next experiment the same basic design was used, but this time drug treatment was given in the drinking water (TX, 100 μg/ml and TO, 400 μg/ml) starting 2 days prior to tumor injection and maintained throughout the experiment. Again, some of the groups received tumor cells mixed with LAK cells at 1:25 ratio and treated further with the same dose of LAK cells injected to the tumor site weekly for 3 weeks. This time significant tumor inhibition occurred in the animals treated with either drug alone and also in those receiving LAK cells only, as can be seen FIG. 3. Again, tumor growth was the slowest in those groups with both drug and LAK treatment. Moreover, there is one animal in the TX+LAK group and also in the TO and TO+LAK group which is tumor free at this time, as can be seen in FIG. 4 a, b and c. Therefore, with continuous treatment we succeeded in slowing tumor growth considerably although the proportion of tumor free animals did not increase.

Example 4.

Figure 5:
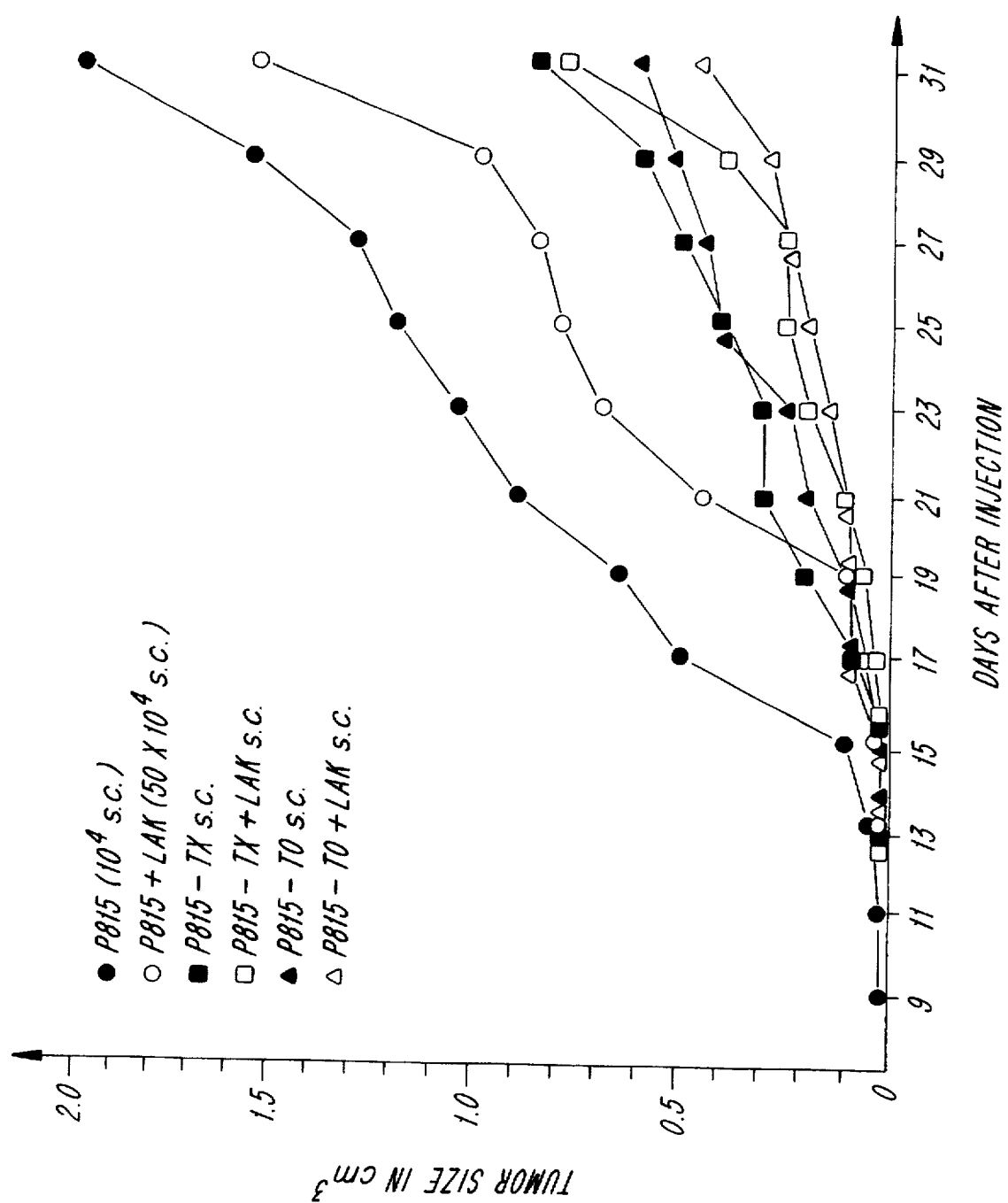
FIG. 5 is a graph of a winn assay with untreated, tamoxifen (TX) treated and toremifene (TO) treated P815 tumor cells.
Figure 6:
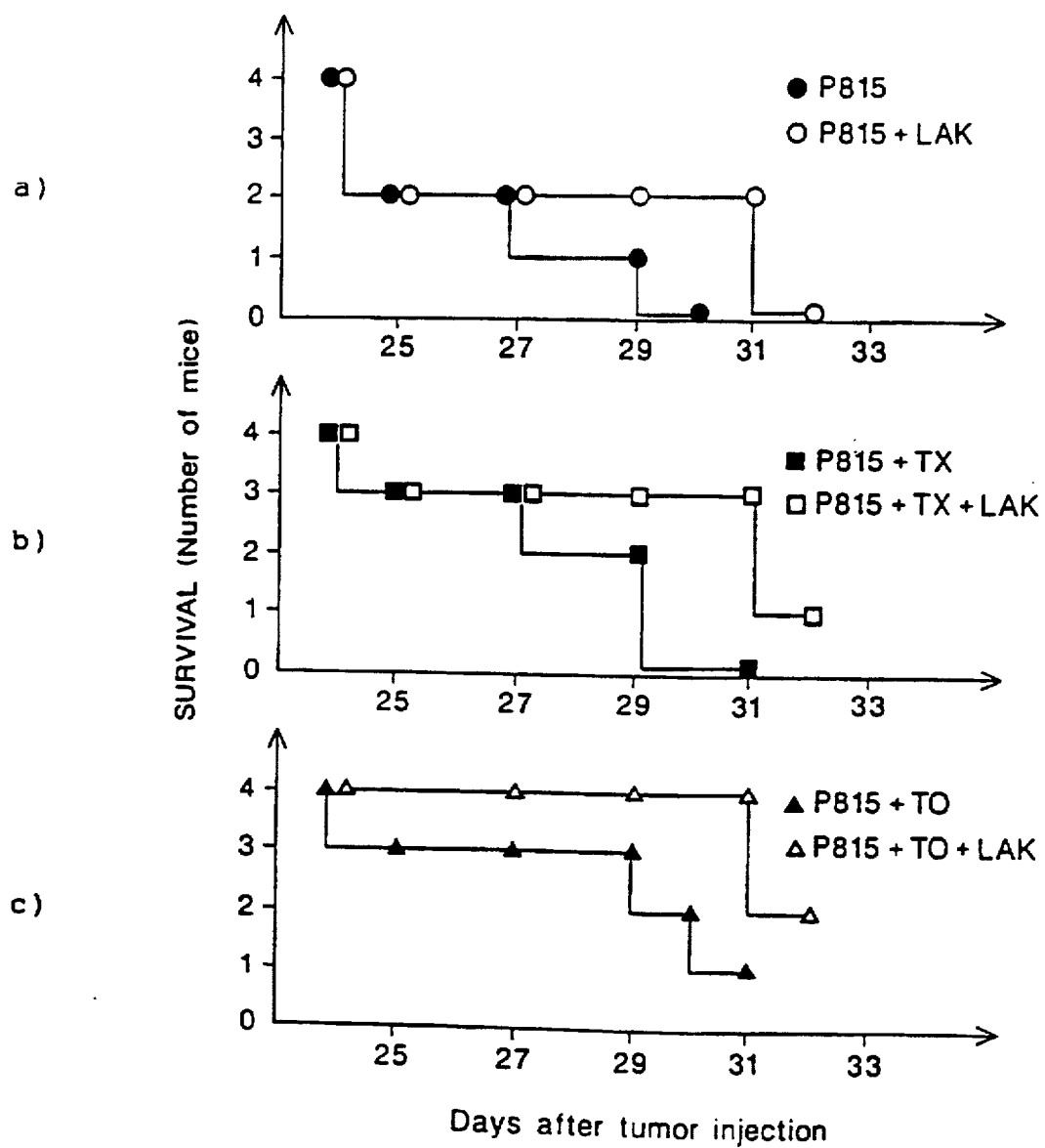
FIGS. 6a, 6b and 6c are the survival curves for the experiment of FIG. 5.

The experiment of Example 2 was repeated with increased amount of LAK cells (1:50 ratio) mixed with drug treated or nontreated tumor cells and applied s. c. to animals. The results are shown in FIG. 5. The survival curves for FIG. 5 are shown in FIG. 6a, b and c. Again, as in previous experiments, there are some tumor free animals in the treated groups, especially when drug treatment is combined with killer cells.

Example 5.

Figure 7:
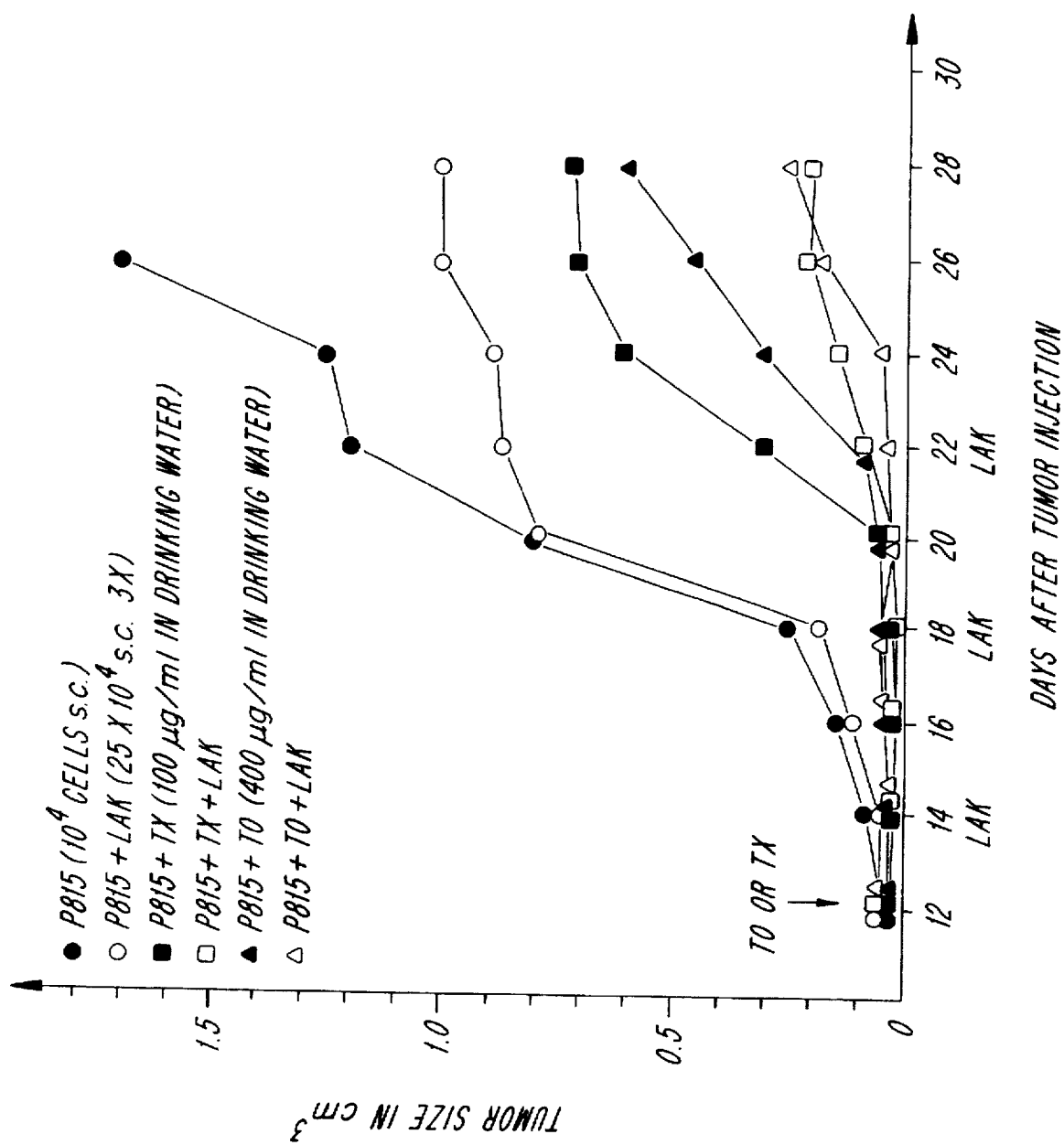
FIG. 7 is a graph demonstrating the immunotherapy results of P815 mastocytoma with TX or TO and LAK cells.
Figure 8:
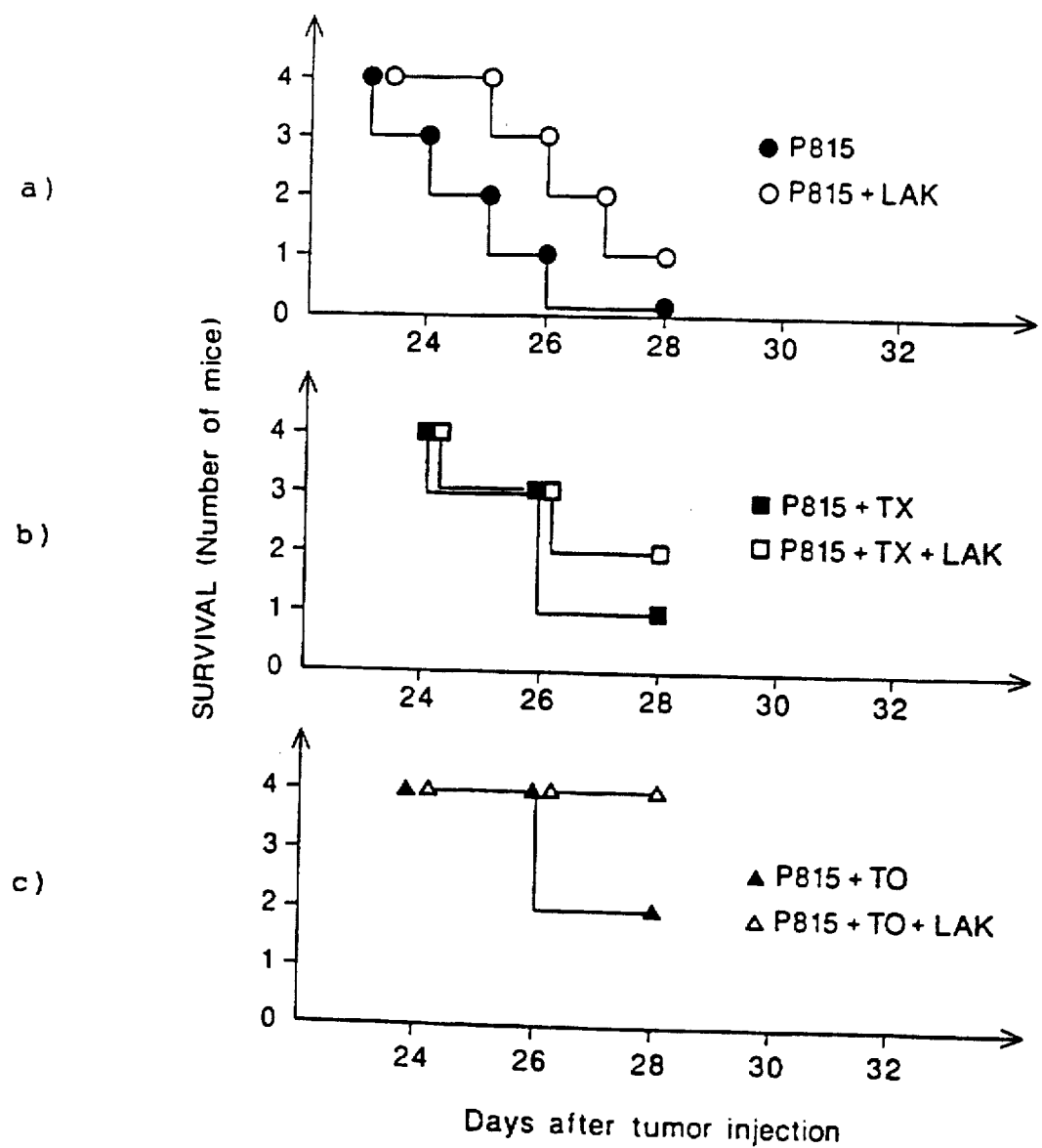
FIGS. 8a, 8b and 8c are the survival curves for the experiment of FIG. 7.

In this immunotherapy experiment all groups received the same dose of tumor cells s. c. and 12 days later when the tumor was clearly palpable in all animals, drug treatment in the drinking water was initiated. Treatment with LAK cells was started 2 days later and given 3 times, 4 days apart, as indicated in FIG. 7. Drug treatment was maintained throughout the experiment. As is obvious from FIG. 7, tumor growth was markedly retarded by drug treatment combined with killer cells. This is also reflected in the survival curves, which are presented in FIG. 8a, b and c. All the controls succumbed to neoplasia by day 26, whereas all the animals are still alive on day 28 in the TO+LAK group. There is one total regression in TX+LAK and one partial regression in TO+LAK treated groups (the tumor volume decreased to 10 times less than the original volume).

Example 6.

Figure 9:
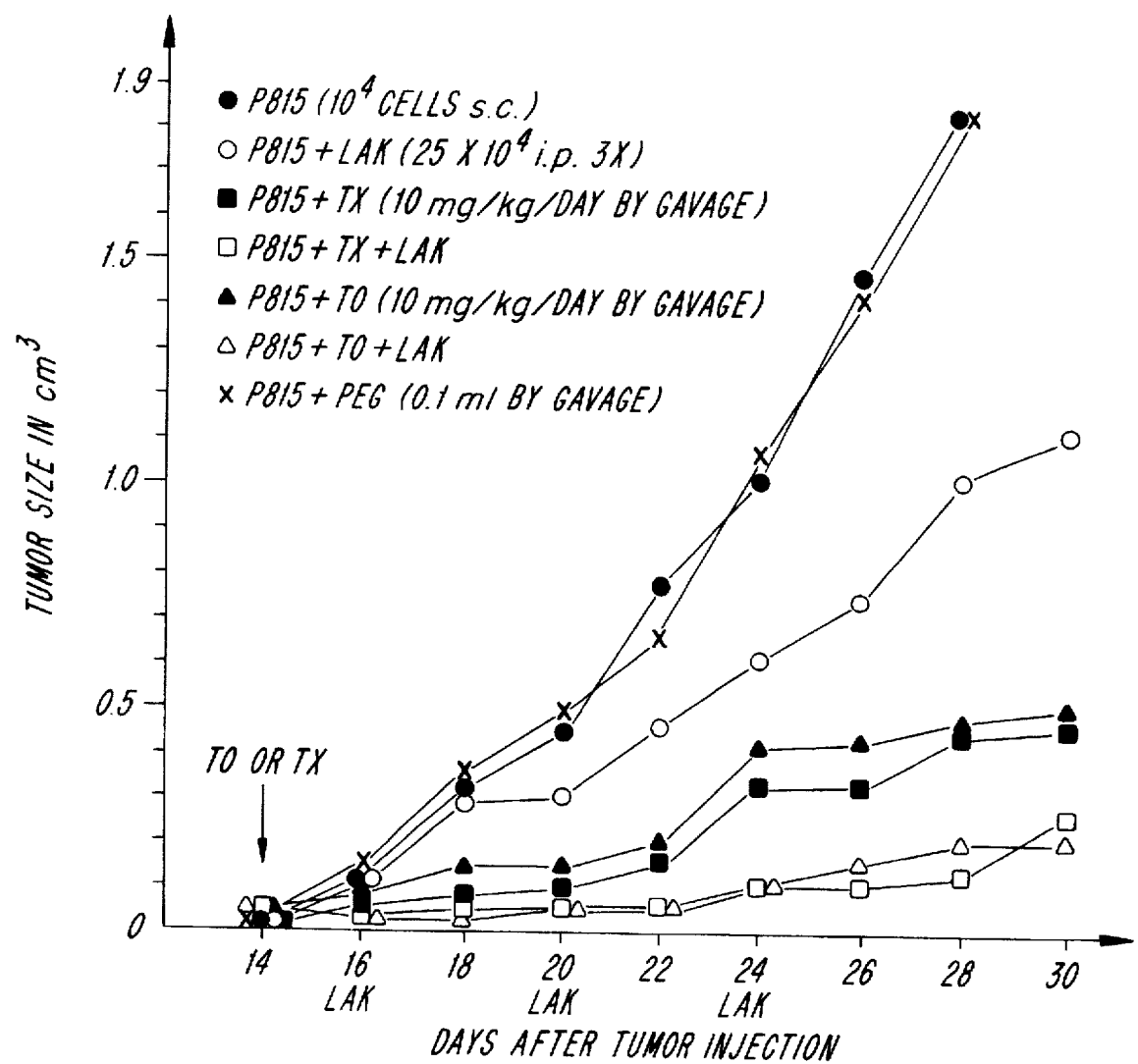
FIG. 9 is a graph demonstrating the immunotherapy results of P815 mastocytoma with TX or TO given by gavage and LAK cells.
Figure 10:
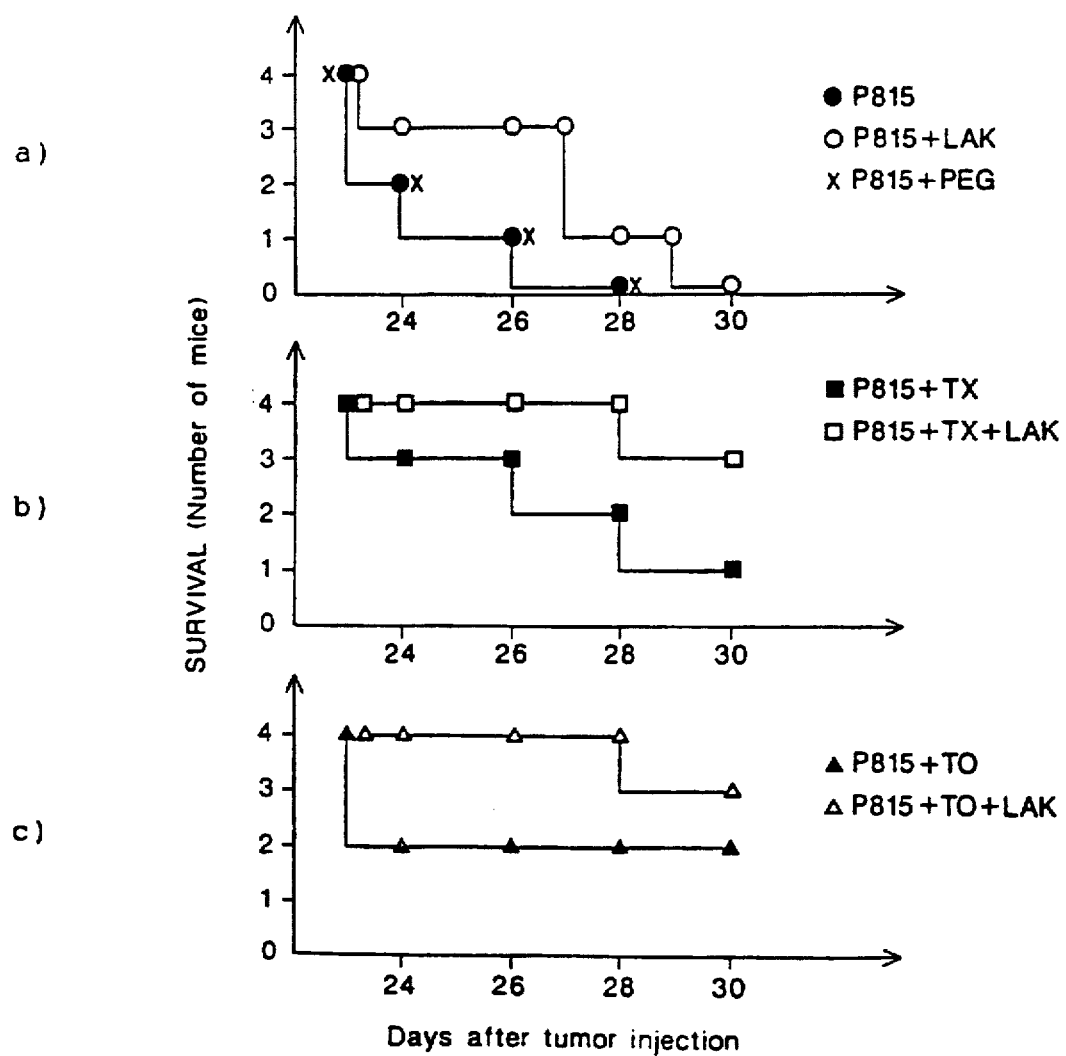
FIGS. 10a, 10b and 10c are the survival curves for the experiment of FIG. 9.

DBA/2 female mice were injected s. c. with $10^4$ P815 tumor cells. When the tumors were approximately 0.5 cm diameter, drug treatment was introduced (either TX or TO, 10 mg/kg/day by gavage). Two days later 25×10⁴ LAK cells were given i.p., LAK was injected three times more, four days apart. Drug treatment was maintained from day 14 until day 30. The results are shown in FIG. 9. Again, tumor growth was markedly retarded by drug treatment combined with killer cells. The survival curves are presented in FIG. 10 a, b and c. There was one total regression in TX+LAK and one partial regression in TO+LAK treated group (the tumor volume decreased to 10 times less than the original volume). Furthermore there was one partial regression both in TX group and TO group.

References Anderson M. et al., J. Natl. Cancer Inst. , 83, 1013–1017, 1991.

Freshney R., Monolayer cultures, In: Human tumours in short term culture. Techniques and clinical applications, PP Dendy, ed. Academic Press, London, 1976.

Fujimoto S. et al., Hum. Cell., 5, 247–55, 1992.

Hietanen T. et al., Breast Res. Treat., 16(Supp), S37–S40, 1990.

Rosenberg S. et al., N. Eng. J. Med., 316, 889–97, 1987.

Yoshino I. et al., Cancer Res., 51, 1494–8, 1991.

Hoover H. et al., J. Clin. Oncol., 11, 3, 390–9, 1993.

Chang A. et al., Cancer Res., 53, 5, 1043–50, 1993.

Livingston P., Curr. Opin. immunol., 4, 5, 624–9, 1992.

Komatsumoto M. et al., Cancer Immunol. Immunother., 33, 279–84, 1991.

Stoychkov J. and Kassabov K., Cancer Immunol. Immunother., 33, 307–313, 1991.

Saarloos M. et al., Cancer Res., 52, 23, 6452–62, 1992.

Aso H. et al., Microbiol Immunol., 36, 10, 1087–97, 1992.

Utsugi T. et al., Cancer Immunol. Immunother., 33, 285–292, 1991.

Gergely P. et al., Acta Med. Hung., 45, 3-4, 307–11, 1988.

We claim:

1. A method for inducing or enhancing killer cell mediated lysis of cancer cells which do not express estrogen receptors (ER-) in a cancer patient comprising administering to said cancer patient (i) an effective amount of a triphenylethylene antiestrogen, and (ii) an effective amount of killer cells selected from the group consisting of NK cells, LAK cells and CTL cells, wherein the administration of (i) said triphenylethylene antiestrogen and (ii) said killer cells is effected jointly or sequentially, and wherein the amount of said triphenylethylene antiestrogen and said killer cells is effective to induce or enhance killer cell mediated lysis of cancer cells which do not express estrogen receptors which are contained in said patient, and further wherein the amount of said triphenylethylene antiestrogen relative to said killer cells is sufficient to sensitize said cancer cells which are contained in said patient such that greater numbers of said cancer cells are lysed by killer cell mediated lysis in comparison to when either said killer cells or antiestrogen are administered singularly.

2. The method of claim 1, wherein said triphenylethylene antiestrogen is selected from the group consisting of tamoxifen, toremifene and pharmaceutically acceptable salts thereof.

3. The method of claim 2, wherein said triphenylethylene antiestrogen is tamoxifen or a pharmaceutically acceptable salt thereof.

4. The method of claim 2, wherein said triphenylethylene antiestrogen is toremifene or a pharmaceutically acceptable salt thereof.

5. The method of claim 3, wherein said tamoxifen or pharmaceutically acceptable salt is orally administered at a daily amount ranging from about 20 to 40 mg.

6. The method of claim 4, wherein said toremifene or pharmaceutically acceptable salt is orally administered in a daily amount ranging from about 40 to 240 mg.

7. The method of claim 1, wherein said method results in tumor inhibition.

8. The method of claim 7, wherein said method results in greater tumor inhibition that when the same amount of triphenylethylene antiestrogen or killer cells is administered singularly.

9. The method of claim 1, wherein said LAK cells are administered daily at a dosage of about 10×10⁸ to 1×10¹⁰ cells.

10. A method for inducing or enhancing killer cell mediated lysis of cancer cells which do not express estrogen receptors in a cancer patient comprising the following steps:
   (i) stimulating the immune system of a cancer patient to induce or enhance the number of killer cells produced by said cancer patient by admininistering an agent that stimulates the immune system; and
   (ii) administering to said cancer patient an amount of a triphenylethylene antiestrogen which is sufficient to induce or enhance killer cell mediated lysis of cancer cells which do not express estrogen receptors which are contained in said patient and further wherein the amount of said triphenylethylene antiestrogen is sufficient to sensitize said cancer cells which are contained in said patient such that greater numbers of said cancer cells are lysed by killer cell-mediated lysis in comparison to when said triphenylethylene antiestrogen or said killer cell stimulation is administered or effected singularly.

11. The method of claim 10, wherein said triphenylethylene antiestrogen is selected from the group consisting of tamoxifen, toremifene and pharmaceutically acceptable salts thereof.

12. The method of claim 10, wherein the immune system of said cancer patient is stimulated to produce killer cells by a method selected from the group consisting of treatment with cyclophosphamide, administration of antigen, administration of cytokine, administration of adjuvant, and administration of vitamin A.

13. The method of claim 10, wherein the immune system of said cancer patient is stimulated to produce killer cells by the administration of IL-2.

14. The method of claim 11, wherein the immune system of said cancer patient is stimulated to produce killer cells by the administration of IL-2.

15. A method for enhancing killer cell mediated lysis of tumor cells which do not express estrogen receptor (ER-) in a cancer patient comprising:
   (i) detecting the presence or absence of killer cells in a cancer patient which are capable of lysing tumor cells which do not express estrogen receptors in said patient; and
   (ii) if said killer cells are present, administering to said cancer patient an amount of at least one triphenylethylene antiestrogen which is sufficient to enhance killer cell mediated lysis of said tumor cells in said patient.

16. The method of claim 1, wherein the killer cells are natural killer (NK) cells.

17. The method of claim 11, wherein the killer cells are lymphokine activated killer (LAK) cells.

18. The method of claim 1, wherein the killer cells are cytotoxic T lymphocyte (CTL) cells.

19. The method of claim 10, wherein the killer cells are natural killer (NK) cells.

20. The method of claim 10, wherein the killer cells are cytotoxic T lymphocyte (CTL) cells.

21. The method of claim 10, wherein the killer cells are lymphokine activated killer (LAK) cells.

22. The method of claim 1, which further includes an in vitor assay prior to treatment to determine weather the patient harbors killer cells capable of destroying his/her cancer cells.

23. The method of claims 22, wherein said in vitro assay comprises obtaining a suspension of tumor cells obtained from the patient and contacting the tumor cells with killer cells obtained from the patient in a cytotoxicity assay.

24. The method of claim 22, which further includes an in vitro assay prior to treatment to determine whether the tumor cells obtained from the patient can be lysed after treatment with triphenylethylene antiestrogens by autologous killer cells.

25. The method of claim 24, wherein said further in vitro assay comprises obtaining a suspension of tumor cells form the patient, pretreating the tumor cells with a triphenylethylene antiestrogen and contacting the pretreated tumor cells with killer cells obtained from the patient in a cytotoxicity assay.

* * * * *